(12) United States Patent
Schwinn

(10) Patent No.: US 6,921,773 B2
(45) Date of Patent: Jul. 26, 2005

(54) USE OF α-1AR SUBTYPE-SELECTIVE DRUGS IN PATIENTS WITH ACUTE MYOCARDIAL INFARCTION

(75) Inventor: Debra A. Schwinn, Durham, NC (US)

(73) Assignee: Duke University, Durham, NC (US)

( * ) Notice: Subject to any disclaimer, the term of this patent is extended or adjusted under 35 U.S.C. 154(b) by 419 days.

(21) Appl. No.: 09/731,062

(22) Filed: Dec. 7, 2000

(65) Prior Publication Data

US 2001/0031460 A1 Oct. 18, 2001

Related U.S. Application Data

(60) Provisional application No. 60/169,294, filed on Dec. 7, 1999.

(51) Int. Cl.$^7$ .......................... A01N 43/26; A61K 31/00
(52) U.S. Cl. ........................................... 514/442; 514/1
(58) Field of Search ..................................... 514/442, 1

(56) References Cited

U.S. PATENT DOCUMENTS 5,767,155 A 6/1998 Chien et al.

FOREIGN PATENT DOCUMENTS

WO WO 98/15272 4/1998

OTHER PUBLICATIONS

O'Malley MK, McDermott EW, Mehigan D, O'Higgins NJ. Role for prazosin in reducing the development of rabbit intimal hyperplasia after endothelial denudation. Br J Surg. 1989 Sep;76(9):936–8.*
Chen and Gardner, "Retinoic Acid Uses Divergent Mechanisms to Activate or Suppress Mitogenesis in Rat Aortic Smooth Muscle Cells", J. Clin. Invest. 102(4):653–662 (1998).
Braunhut and Moses, "Retinoids Modulate Endothelial Cell Production of Matrix–degrading Proteases and Tissue Inhibitors of Metalloproteinases (TIMP)", The Journal of Biological Chemistry 269(18):13472–13479 (1994).
Davidson et al, "Ascorbate Differentially Regulates Elastin and Collagen Biosynthesis in Vascular Smooth Muscle Cells and Skin Fibroblasts by Pretranslational Mechanisms", The Journal of Biological Chemistry 272(1):345–352 (1997).
Kagan, "Intra– and extracellular enzymes of collagen biosynthesis as biological and chemical targets in the control of fibrosis", Acta Tropica 77:147–152 (2000).
Kivirikko and Myllyharju, "Prolyl 4–Hydroxylases and their Protein Disulfide Isomerase Subunit", Matrix Biology 16:357–368 (1998).
Schwinn et al, "Cloning and Pharmacological Characterization of Human Alpha–1 Adrenergic Receptors: Sequence Corrections and Direct Comparison with Other Species Homologues", The Journal of Pharmacology and Experimental Therapeutics 272(1):134–142 (1995).
Gregorini et al, "αAdrenergic Blockade Improves Recovery of Myocardial Perfusion and Function After Coronary Stenting in Patients With Acute Myocardial Infarction", Circulation 99(4):482–490 (1999).
Razik et al, "Transcriptional Regulation of the Human $α_{1a}$–Adrenergic Receptor Gene", The Journal of Biological Chemistry 272(45):28237–28246 (1997).
Hoehe et al, "A two–allele PstI RFLP for the alpha–1C adrenergic receptor gene (ADRA1C)", Human Molecular Genetics 1(5):349 (1992).
Hoehe et al, "Genetic mapping of adrenergic receptor genes in humans", J Mol. Med. 73:299–306 (1995).
Andersson et al, "Prostatic $α_1$–Andrenoceptors and Uroselectivity", The Prostate 30:202–215 (1997).
Docherty, "Subtypes of functional $α_1$–and $α_2$–adrenoceptors", European Journal of Pharmacology 361:1–15 (1998).
Richardson et al, "Pharmacology of Tamsulosin: Saturation–Binding Isotherms and Competition Analysis Using Cloned $α_1$–Adrenergic Receptor Subtypes", The Prostate 33:55–59 (1997).
Michel and Rump, "alpha–Adrenergic regulation of human and renal function", Fundamental & Clinical Pharmacology 10(6):493–503 (1996)—Abstract.
Docherty and O'Rourke, "The α–Adrenoceptor–Mediated Actions of Chloroethylclonidine", Gen. Pharmac. 28(2):197–201 (1997).
Graham et al, "$α_1$–Adrenergic Receptor Subtypes", Circulation Research 78:737–749 (1996).
Rudner et al, "Subtype Specific Regulation of Human Vascular α1–Adrenergic Receptors by Vessel Bed and Age", Circulation 100:2336–2343 (1999).
Malloy et al, "α1–Adrenergic Receptor Subtypes in Human Detrusor", The Journal of Urology 160:937–943 (1998).

* cited by examiner

Primary Examiner—Joseph Murphy
(74) Attorney, Agent, or Firm—Nixon & Vanderhye P.C.

(57) ABSTRACT

The present invention relates to the use of $α_{1a}$AR-selective and/or $α_{1a}/α_{1d}$-selective antagonists in a method of preventing restenosis after myocardial infarction and re-perfusion. The invention further relates to a method of identifying agents suitable for us in such a method.

4 Claims, 5 Drawing Sheets

Prazosin

5-MU

Spiperone

BMY-7378

USE OF α-1AR SUBTYPE-SELECTIVE DRUGS IN PATIENTS WITH ACUTE MYOCARDIAL INFARCTION

This application claims priority from Provisional Application No. 60/169,294, filed Dec. 7, 1999, the entire content of which is incorporated herein by reference.

This invention was made with Government support under HL49103 awarded by the National Institutes of Health. The Government has certain rights in the invention.

TECHNICAL FIELD

The present invention relates to the use of $\alpha_{1a}$AR-selective and/or $\alpha_{1a}/\alpha_{1d}$-selective antagonists in a method of preventing restenosis after myocardial infarction and re-perfusion. The invention further relates to a method of identifying agents suitable for us in such a method.

BACKGROUND

Alpha$_1$-adrenergic receptor ($\alpha_1$AR) stimulation mediates sympathetic nervous system responses such as vascular smooth muscle contraction and myocardial hypertrophy. $\alpha_1$AR-mediated vasoconstriction contributes to baseline (tonic) vessel tone, modulates systemic vascular resistance/venous capacitance, and is important in cardiovascular responses to shock.[1] in addition, during "fight and flight" responses, elevated catecholamines result in constriction of "nonessential" vascular beds (e.g. splanchnic) while blood flow to vital organs (e.g., brain, heart) remains uncompromised.[2,3] cDNAs encoding three human $\alpha_1$AR subtypes ($\alpha_{1a}$, $\alpha_{1b}$ and $\alpha_{1d}$[4,5]) were recently cloned, each expressed receptor pharmacologically characterized,[4] and species heterogeneity in $\alpha_1$AR subtype tissue distribution identified.[6,7] All three $\alpha_1$ARs couple predominantly via Gq to phospholipase C-b activation, resulting in formation of inositol trisphosphate (IP$_3$), calcium release from intracellular stores, and ultimately to smooth muscle contraction.[8]

Although reasons for existence of three $\alpha_1$AR subtypes remain elusive, recent findings suggest subtype and tissue specific regulation may be important.[9,10] While all $\alpha_1$AR subtypes mediate smooth muscle contraction, hypertrophic pathways demonstrate subtype specific signaling.[11] $\alpha_1$AR agonist exposure to neonatal rat myocytes results in $\alpha_{1a}$AR mRNA/protein upregulation (doubling) concurrent with $\alpha_{1b}$ and $\alpha_{1d}$ downregulation, correlating with induction of myocardial hypertrophy.[12] In contrast, insulin and insulin-like growth factor I induces $\alpha_{1d}$AR expression in cultured rat vascular smooth muscle cells.[13] Hence agonist exposure, disease states, and drugs alter $\alpha_1$AR subtype expression.

The present invention results, at least in part, from studies designed to determine the mechanisms underlying cardiovascular responses to acute stress and chronic catecholamine exposure (e.g. aging). Human vascular $\alpha_1$AR subtype distribution and function were examined. Specifically, two hypotheses were tested: 1) human $\alpha_1$AR subtype expression differs with vascular bed, and 2) age influences human vascular $\alpha_1$AR subtype expression. The results demonstrate human vascular $\alpha_1$AR subtype distribution differs from animal models, varies with vessel bed, correlates with contraction in mammary artery, and is modulated by aging.

SUMMARY OF THE INVENTION

The present invention relates to the use of $\alpha_{1a}$AR-selective and/or $\alpha_{1a}/\alpha_{1d}$-selective antagonists in a method of preventing restenosis after myocardial infarction and re-perfusion. The invention further relates to a method of identifying agents suitable for us in such a method.

Objects and advantages of the present invention will be clear from the description that follows.

DETAILED DESCRIPTION OF THE INVENTION

Figure 1A:
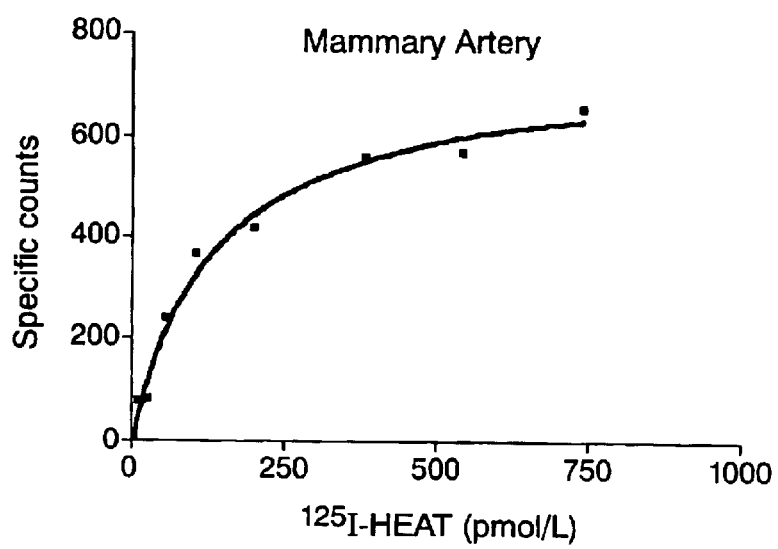
FIGS. 1A–1C—Representative saturation binding isotherms for human mammary artery (FIG. 1A), aorta (FIG. 1B), saphenous vein (FIG. 1C).

The present invention results, at least in part, from studies designed to characterize a$_1$AR subtype distribution in humans across different vascular beds. The results presented in the Example that follows demonstrate a$_1$AR subtype expression varies according to vessel bed. Specifically, a$_{1a}$AR mRNA/protein predominates in coronary, splanchnic, renal, and pulmonary arteries, whereas central arteries and veins express all 3 a$_1$ARs. With aging (<55 versus ≧65 years), a two-fold increase in overall mammary artery (but not saphenous vein) a$_1$AR expression occurs (a$_{1b}$>a$_{1a}$). Robust $\alpha_{1a}$ and $\alpha_{1b}$-mediated contraction for all ages studied indicate these findings have functional significance.

$\alpha_1$AR-mediated smooth muscle contraction is important in determining tonic and reflex changes in arterial and venous diameter. Instantaneous changes in vessel tone are responsible for maintenance of blood pressure and venous return to the heart during stress (e.g. hypovolemia [hemorrhage], shock, and sepsis).[1] At rest, adult splanchnic vessels contain 30% total circulating blood volume;[3] acute sympathetically-mediated constriction is a primary mechanism underlying maintenance of blood pressure during shock or hemorrhage. Robustness of compensatory mechanisms is illustrated by blood pressure stability until >20% blood volume is lost.[18]

Vascular $\alpha_1$ARs have been studied in animals using a variety of techniques (Table 5). After initial controversy, it has been generally agreed $a_{1d}$ARs mediate vasoconstriction in rat aorta;[15,19] in contrast, contraction in dog, rabbit, and mouse aorta occurs via $a_{1b}$ARs.[20-22] $a_1$AR subtype-mediated contraction also differs along mesenteric bed; $a_{1d}$AR mediates contraction in rat superior mesenteric artery (proximal) whereas $a_{1b}$ARs function in distal mesenteric arteries.[19] Only a few studies in human vessels have been performed to date; these identify all three $a_1$AR subtype mRNAs in human mesenteric artery,[23] $a_{1b}$ and $\alpha_{1d}$ in human aorta,[6] and $a_{1a}$ in saphenous vein[24] and vena cava.[6] $a_{1b}$-mediated contraction occurs in human superior vesicle and obturator arteries,[25] and $a_{1a}$-mediated contraction in human mesenteric artery.[26] The findings further indicate that $\alpha_{1a}$AR-mediated contraction accounts for generalized splanchnic vasoconstriction during stress in humans, although this hypothesis must be confirmed by further contraction studies. Other findings of clinical relevance include $a_1$ARs in renal, pulmonary, and coronary vasculature as possible targets for treatment of renal insufficiency, pulmonary hypertension, and angina. Since veins contain all three $a_1$AR subtypes, pharmacological isolation preload (venous return) and afterload (arterial vascular resistance) is possible. While the experiments described in the Examples that follow utilized "normal" vessels, examination of alterations of $a_1$AR subtype distribution by disease can be made.

Sympathetically-mediated vascular responsiveness changes with age, although precise mechanisms underlying this observation remain unknown.[8] While overall aortic $a_1$AR density remains unchanged with age in rat, subtype modulation occurs (increased $a_{1a}$, decreased $\alpha_{1b}$, unchanged $\alpha_{1d}$);[27] other studies suggest age decreases all $a_1$ARs in rat,[28] but increases in sheep.[29] Age-related changes are vessel specific, with rat renal $\alpha_{1b}$AR mRNA declining without change in mesenteric/pulmonary $a_1$ARs.[28] Furthermore, age increases functional $a_{1d}$ARs in resistance vessels compared with $a_{1a}$AR predominance in young rats.[30] In humans, age increases in-hospital mortality associated with major surgery;[31] risks include vascular-associated conditions such as gastrointestinal infarction and limb ischemia.[2,32,33] The results reveal age-related increases in mammary artery $a_1$AR density (but not saphenous vein), and a switch from $a_{1a}$ predominance in younger adults to $a_{1b} > a_{1a}$ in older patients. Other arteries need to be tested to determine whether age-induced arterial changes are global, or mammary artery specific. In support of a global interpretation of the present findings, a recent clinical study demonstrates less blood pressure perturbation in elderly patients with tamsulosin ($a_{1a}/a_{1d}$-selective antagonist) compared with alfuzosin (non-selective),[34] indicating importance of $a_{1b}$ARs with aging in resistance vessels.

The result presented herein demonstrate human vascular $\alpha_1$AR subtype distribution differs from animal models, varies with vessel bed. correlates with contraction in mammary artery, and is modulated by aging. This information provides targets for therapeutic intervention in a clinical settings.

Certain aspects of the present invention are described in greater detail in the Example that follows.

EXAMPLES

Methods
Human Vessels

Vessels were obtained after approval from the Duke University institutional review board and individual agencies. Sources included discarded tissues from surgery (0–60 minutes from isolation), Duke University rapid autopsy program (0–3 hours postmortem), National Disease Research Interchange (Philadelphia, Pa.; 0–5 hours postmortem), and the International Institute for the Advancement of Medicine (Scranton, PA; within 12 hours postmortem). Except for functional assays, vessels were snap frozen in liquid nitrogen and stored at −70° C. for later use.

Membrane Preparation and Radioligand Binding

Vessels were weighed, lumen diameter measured, pulverized under liquid nitrogen, and suspended in cold lysis buffer (5 mmol/L Tris HCl and 5 mmol/L EDTA, pH 7.4) with protease inhibitors.[14] After lysate preparation, membranes were resuspended in cold binding buffer (150 mmol/L NaCl, 50 mmol/L Tris·HCl, 5 mmol/L EDTA, with protease inhibitors, pH 7.4) as previously described;[14] protein concentration was determined using the bicinchoninic acid method (Pierce, Rockford, Ill.). Full saturation binding isotherms were performed in selected human vessels (aorta, mammary artery, saphenous vein) in 250 $\mu$l binding buffer (20–60 $\mu$g vessel membrane protein) using the $\alpha_1$-adrenergic antagonist [$^{125}$I]HEAT(2-[b-(hydroxy-3[$^{125}$I]iodophenyl) ethyl-aminomethyl]-tetralone; DuPont-NEN; Boston, Mass.) as previously described.[14] To measure total $a_1$AR density in all vessels, a saturating concentration (300 pmol/L) of the [$^{125}$I]HEAT was used. A Kd concentration (130 pmol/L [$^{125}$I]HEAT) was used in competition analysis with antagonists 5-MU WB4101, and BMY7378 ($10^{-12}$ to $10^{-4}$ mol/L).

RNase Protection Assays (RPAs)

RNA isolation and human $a_1$AR cDNA constructs have previously been described.[14] RPAs were performed as previously described; control b-actin consisted of 0.104 kb (HinP1I/TaqI) fragment in pGEM-4Z (GenBank #AB004047; nucleotide 119–222).[14] [$^{32}$P]aCTP (DuPont-NEN) was incorporated into RNA probes at the time of synthesis. After digestion with RNase A and T1, RNA samples were separated electrophoretically through a 6% polyacrylamide gel, dried, and exposed to X-Omat film (Eastman Kodak Company; Rochester, N.Y.) for 18–24 hours, and Phosphorimager plates (Molecular Dynamics: Sunnyvale, Calif.) for 72 hours. Volume integration of protected fragments was corrected for background using ImageQuant image analysis software (Molecular Dynamics) and counts were normalized for b-actin signal and $^{32}$P-aCTP incorporation (CTPs: $a_{1a}$—97, $a_{1b}$—219, $a_{1d}$—133). Final mRNA data are scaled +1 to +10, with +10 (100 arbitrary units) assigned $a_{1a}$AR mRNA in liver (human tissue known to contain maximal $a_1$AR mRNA); thus Phosphorimager counts/10,000×1.8 defined Phosphorimager units. $a_{1a}$AR mRNA is highest in mesenteric artery (26 units): therefore, +3=20–29 units; +2=10–19 units; +1=4–9 units; (−)=almost undetectable signal ($\leq$3 units) Phosphorimager, negative autoradiograph; −=lack of signal on both.

Functional Assays

Since the presence of receptor protein does not always correlate with functional response,[15] $a_1$AR-mediated contractility in mammary artery was tested using phenylephrine dose response curves in the absence/presence of subtype selective/nonselective antagonists. Mammary arteries were immersed in cold oxygenated Krebs-Ringer bicarbonate solution (118.3 mmol/L NaCl, 4.7 mmol/L KCl, 1.2 mmol/L MgSO$_4$, 1.2 mmol/L KHPO$_4$, 42.5 mmol/L CaCl$_2$, 25 mmol/L NaHCO$_3$, 16 mmol/L CaEDTA, 1.1 mmol/L glucose), cleaned of loose connective tissue, cut into 4–5 mm long rings, and suspended for isometric tension recording in organ chambers. One stirrup was anchored to the chamber and the other connected to a strain gauge (FT-102) for measurement of isometric force (MacLab, CB Sciences;

Milford, Mass.). All concentration effect curves were performed at optimum resting tone (~3 g in pilot studies). Contractile response to 60 mmol/L KCl was performed; this determined vessel viability and facilitated normalization of phenylephrine response across vessel rings. Phenylephrine dose-response curves were generated ($10^{-4}$–$10^{-9}$ mol/L) in ½ log order concentrations in the absence/presence of competitive $a_1$AR antagonists. Contraction assays using vessel rings from an individual patient were performed simultaneously in separate baths for each antagonist; hence each vessel ring was exposed to three dose response curves. Antagonist potency was expressed as the dissociation constant ($K_B$) determined from $pK_B=\log[B]\log(DR-1)$, where [B] is antagonist concentration and DR the dose ratio produced by antagonist. Dose response curves were analyzed using DOSE RESPONSE software (MacLab, CB Sciences).

Statistical Analysis

Data were tested for normal distribution using Shapiro-Wilke test of normality. Overall $\alpha_1$AR density was compared between vessels using a general linear multivariate model, and where significant differences identified between specific vascular beds, the exact p value was determined using Wilke's-Lambda test; $p<0.05$ was considered significant. Since determination of $\alpha_1$AR subtype expression involved three subtypes ($a_{1a}$, $a_{1b}$, $a_{1d}$), critical $\alpha$ was reduced to 0.0167 for these studies. Similarly, when comparing $\alpha_1$AR subtype expression between different vascular beds, pairwise comparisons were made using a Wilcoxon 2-sample rank sum test, and critical $\alpha$ set at 0.0167. Competition binding and functional assays were analyzed using least squares regression analysis with Prism software (GraphPad; San Diego, Calif.). Final data were analyzed using SAS system, release v.6.12 (SAS Institute Inc., Cary, N.C.), and presented as mean±SEM to two significant figures.

Results

Characterization of Human Vessels 500 vessels from 384 patients (male, n=257; female, n=127; 64±0.82 years [range 12–92]) were used. The majority (83%) were collected from operating room specimens, 17% from autopsy (cause of death: gun shot, automobile accident, myocardial infarction, cancer). 95% vessels were obtained ≦3 hours from tissue isolation or death (within 12 hour postmortem mRNA/protein stability period in rats/humans).[16,17] Vessels were obtained only from patients without co-existing disease (e.g. no chronic renal failure, congestive heart failure, diabetes, hypertension, thyroid disease), or potentially confounding drugs (e.g. no estrogen supplementation, catecholamines, sympathetic stimulants, antidepressants, or aAR drugs); five years was required to collect enough vessels to complete the study. Due to limited vessel RNA/protein, n=1 vessel from a single individual whenever possible, but sometimes represents pooled samples from 2–6 patients with similar patient characteristics.

Human Vascular Total $a_1$AR Expression

Figure 1B:
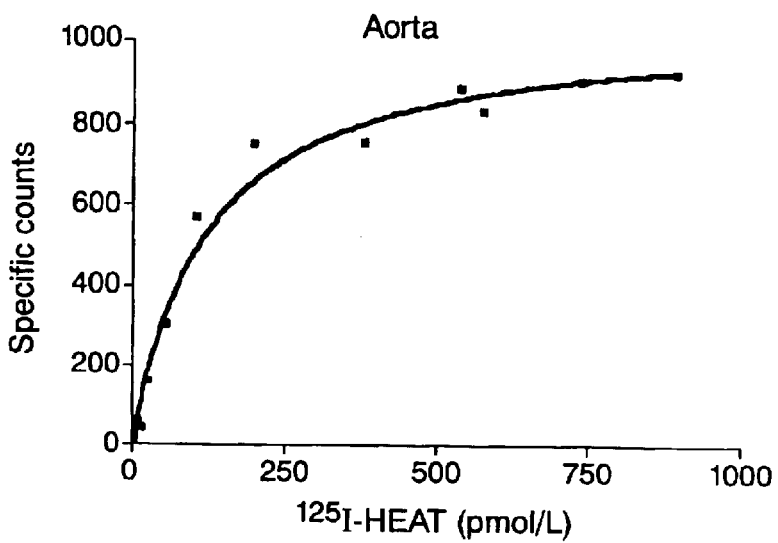
Figure 1C:
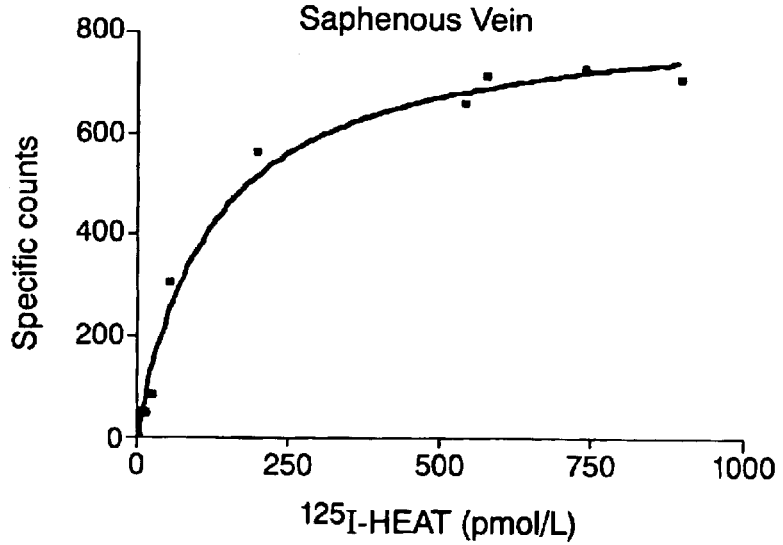

The "fight and flight" (stress) response results in redistribution of blood from splanchnic and "non-essential" organs toward vital organs.[2,3] In order to test the hypothesis that $a_1$AR density in splanchnic versus somatic vessels may be responsible for these effects, Kd and Bmax were determined for $^{125}$I-HEAT binding in selected human vessels (nonspecific binding 30–70%). Kd is 130±0.20 (aorta), 130±3.1 (mammary artery), and 130±0.65 (saphenous vein) pmol/L (n=2–4 each, FIG. 1), similar to cloned human $a_1$ARs.[4] Overall human vascular $a_1$AR expression is 16±2.3 fmol/mg total protein; central (conduit) and small somatic arteries express significantly lower $a_1$AR density than splanchnic arteries, $p<0.05$, Table 1). In contrast, venous $a_1$AR density does not change with vessel diameter or vascular bed.

Figure 2:
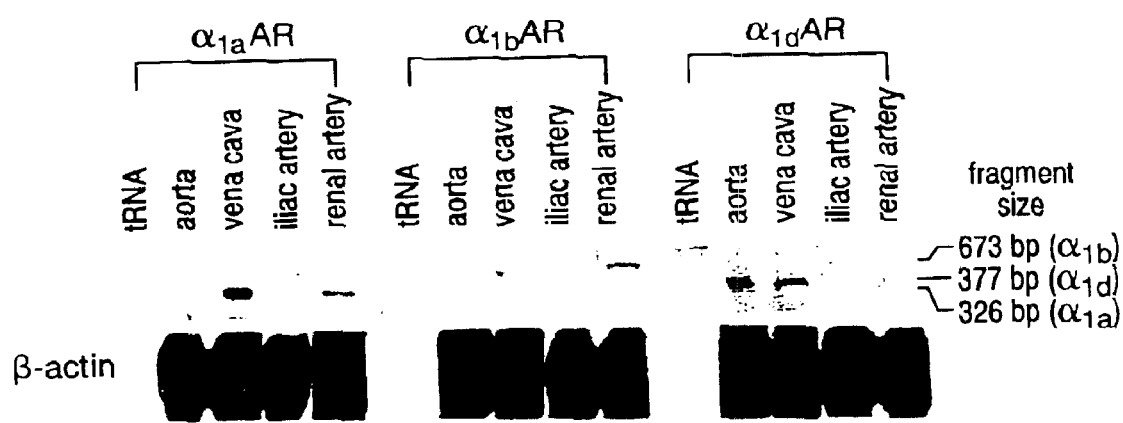
FIG. 2—Representative RNase protection assay. Autoradiograph (24-hour exposure) demonstrating specific hybridization of a$_1$AR subtype radiolabeled antisense riboprobes with total RNA isolated from tRNA (negative control), human aorta, vena cava, iliac artery, and renal artery.
Figure 3A:
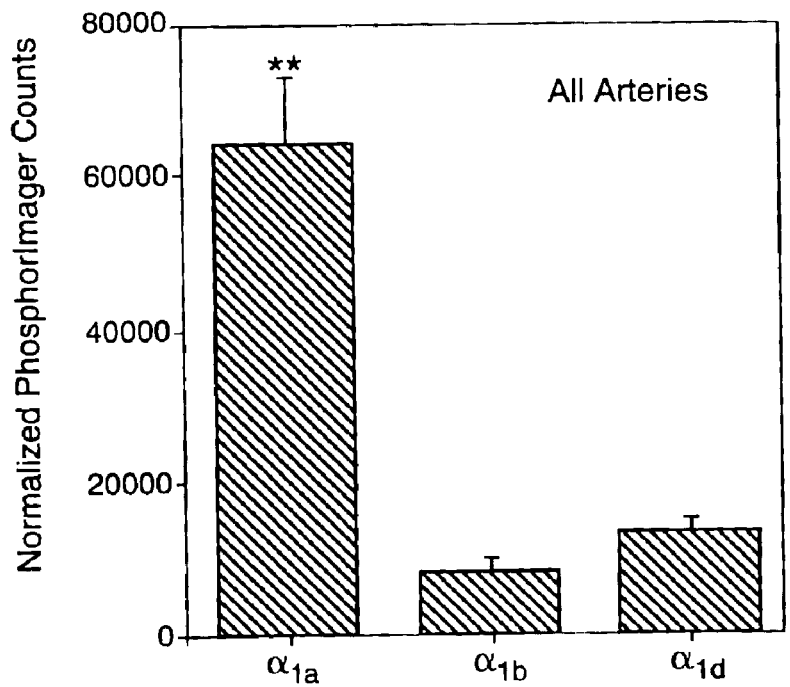
FIGS. 3A and 3B—Phosphorimager counts from RNase protection assays for each a$_1$AR subtype. a$_{1a}$AR mRNA expression is significantly higher overall in arteries (FIG. 3A) compared with a$_{1b}$AR and a$_{1d}$AR (**p<0.001), particularly splanchnic (SPL) versus central arteries (CEN) (*p<0.05) (FIG. 3B).
Figure 3B:
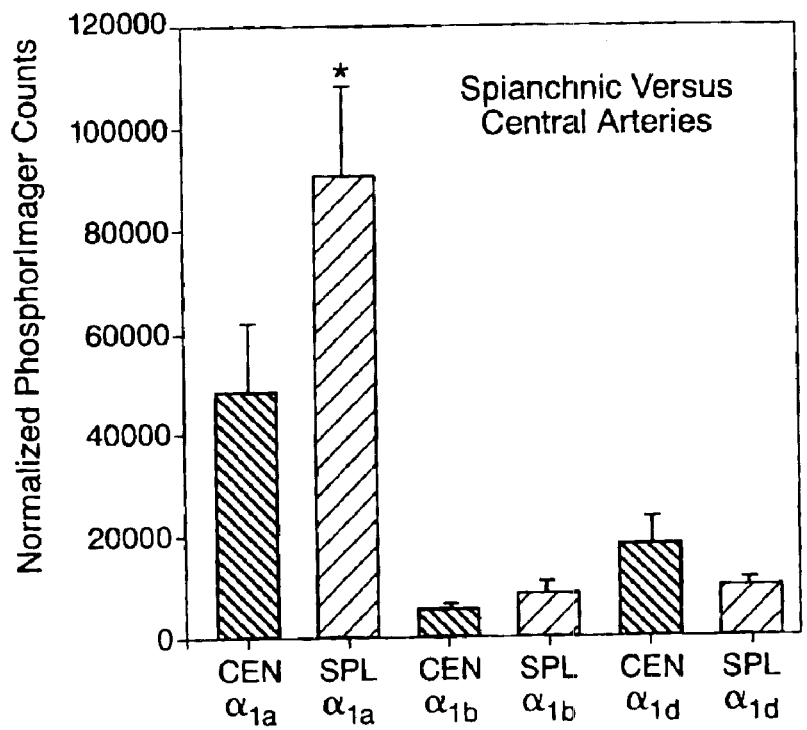
Figure 4A:
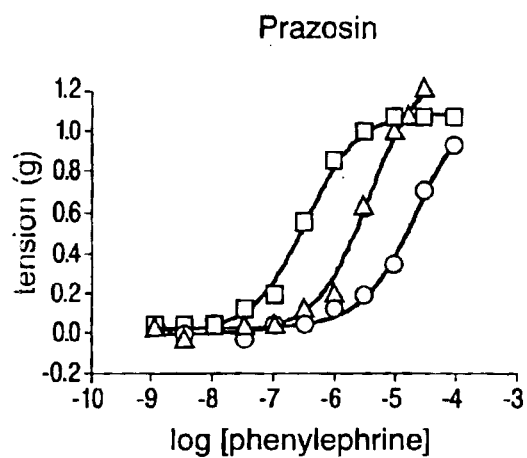
FIGS. 4A–4D—Phenylephrine-induced mammary artery contraction. Antagonists prazosin (nonselective) (FIG. 4A), 5-MU (a$_{1a}$-selective) (FIG. 4B), spiperone (relatively a$_{1b}$-selective) (FIG. 4C) demonstrate concentration dependent shift in potency without reducing maximum response. BMY7378 ($\alpha_{1d}$-selective) (FIG. 4D) does not produce a significant shift. Two concentrations of antagonist are shown: ■ control; ▲ low (prazosin—$10^{-9}$ mol/L; 5-MU/spiperone/BMY7378—$10^{-8}$ mol/L); ● higher (prazosin—$10^{-8}$ mol/L; 5-MU/spiperone/BMY7378—$10^{-7}$ mol/L).
Figure 4B:
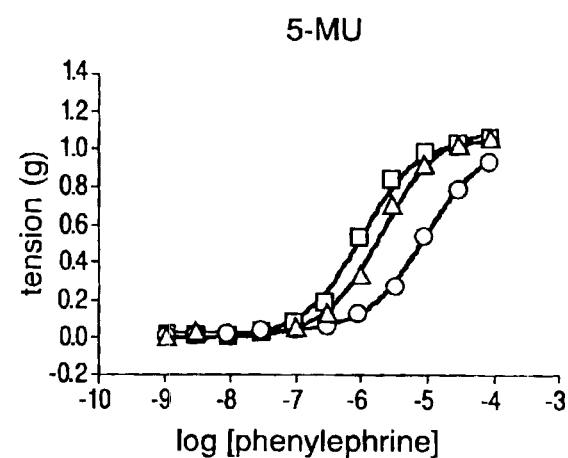
Figure 4C:
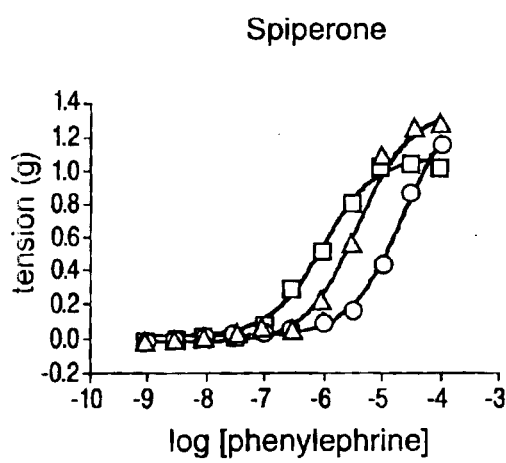
Figure 4D:
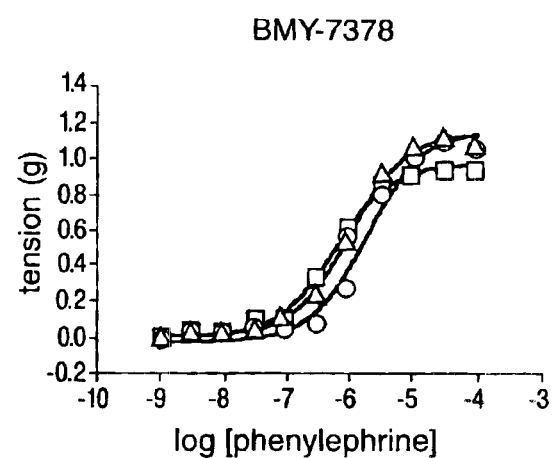
Figure 5B:
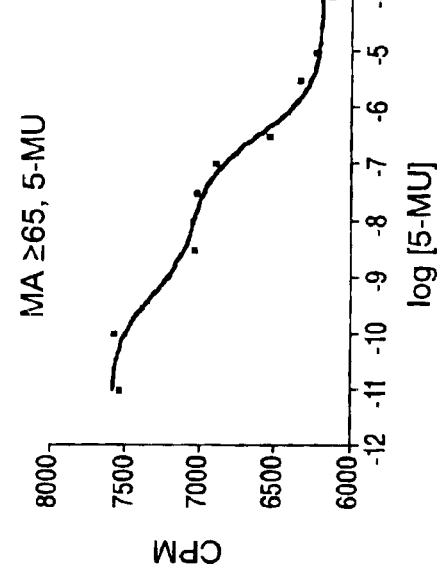
FIGS. 5A–5D—a$_1$AR subtype expression in mammary artery from young (<55 years, n=6) (FIGS. 5A and 5C) versus older (>65 years, n=6) (FIGS. 5B and 5D) patients. Competition analysis with 5-MU (a$_{1a}$>a$_{1b}$=a$_{1d}$) (FIGS. 5A and 5B) or WB4101 (a$_{1a}$=a$_{1d}$>a$_{1b}$) (FIGS. 5C and 5D). See Table 4 for pKi values.
Figure 5D:
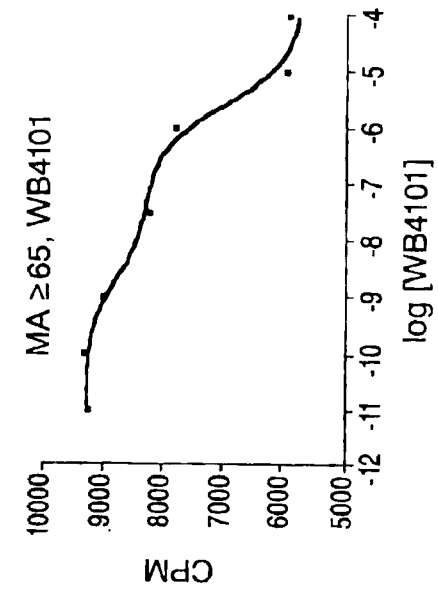
Figure 5A:
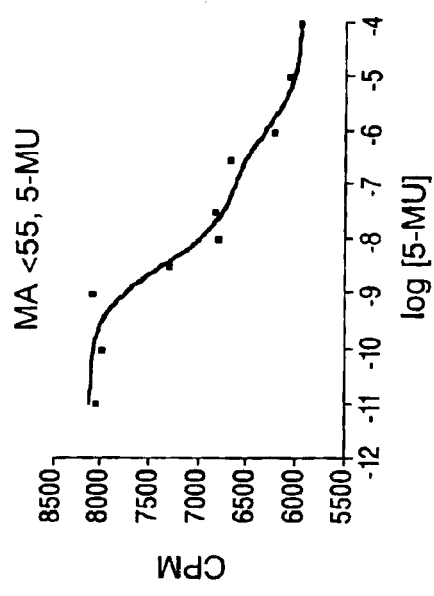
Figure 5C:
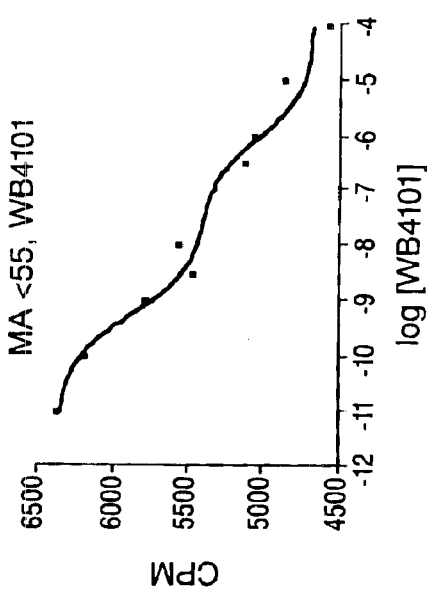

$a_1$AR Subtype mRNA in Human Vessels $a_1$AR subtypes were next examined; due to limited tissue, molecular approaches were utilized. All three $a_1$AR mRNAs are present in human vessels (FIG. 2), with $\alpha_{1a}$AR predominating overall in arteries ($p<0.001$); epicardial coronary arteries express $a_{1a}$ exclusively (Table 2). $\alpha_{1a}$AR subtype density is significantly higher in splanchnic versus central vessels ($p<0.05$; FIG. 3). These findings suggest $a_1$AR subtype expression varies with vessel type.

$a_1$AR Subtype Protein in Human Vessels

To ensure mRNA and protein expression correlate, competition analysis was performed. Selected vessels were chosen for availability and expression of only one or two $\alpha_1$AR subtypes (to facilitate interpretation of results). Since $a_{1a}$AR mRNA predominates, 5-MU ($a_{1a}$-selective antagonist) was utilized. $a_1$AR subtype protein expression in 4 representative human vessels was determined by competition analysis with 5-MU ($a_{1a}$-selective antagonist) (n=3 experiments per vessel, each performed in triplicate); Table 3 summarizes pki values (-logKi; measure of receptor affinity for antagonist). 5-MU binds to two sites in mammary, renal, splenic arteries, and vena cava, with the high affinity pKi site consistent with interactions at cloned $\alpha_{1a}$ARs.[4] Although designation of the high affinity binding site is straightforward, low affinity $\alpha_1$AR site identification was aided by mRNA data in Table 2 and confirmed in mammary artery (and aorta) using BMY7378 ($a_{1d}$-selective antagonist). Only one binding site was detected in aorta, coronary artery, and hepatic artery, with pKi values consistent with $\alpha_{1d}$, $\alpha_{1a}$, and $\alpha_{1a}$ARs, respectively. These data suggest mRNA and protein expression correlate closely in human vessels.

Human Mammary Artery Contraction

Phenylephrine dose response curves were completed in 10 mammary arteries (patient age 60±2.2 years [range 37–73]), vessels which contain only $a_{1a}$ and $a_{1b}$ARs; isometric contraction occurs with $pD_2$ 6.0±0.093. $a_1$AR competitive antagonists produce a concentration dependent shift in potency of phenylephrine contraction without reducing maximum response (FIG. 4). Potency in inhibiting mammary artery contraction ($pK_B$) is 9.2±0.046 (prazosin, non-selective), 8.4±0.63 (5-MU. $a_{1a}$-selective), and 8.6±0.19 (spiperone, relatively $a_{1b}$-selective), similar to affinities for each antagonist at cloned human $a_1$ARs.[4] BMY7378 ($\alpha_{1d}$-selective) does not produce a shift in dose response. These data suggest $a_{1a}$ and $a_{1b}$ARs mediate contraction in human mammary artery.

Regulation of Vascular $a_1$AR Subtype Expression by Age

Mammary artery $\alpha_1$AR density increases significantly with age (4.4±0.78<55 years versus 9.3±1.7≧65 years, p=0.003, fmol/mg total protein) (Table 4). In contrast, saphenous vein $\alpha_1$AR density does not change with age. Competition analysis with 5-MU and WB4101 reveals $\alpha_{1a}$ARs are the major subtype in mammary artery in patients <55 years of age (FIG. 5). However, with aging, $\alpha_{1b}$AR expression significantly increases (3-fold, p=0.0001), becoming the major subtype in patients ≧65 years; $\alpha_{1a}$ARs also significantly increases with age (1.5-fold, p≦0.001). $\alpha_{1d}$AR expression is virtually absent in younger and older patients.

REFERENCES

1. Ruffolo R R, Jr. Distribution and function of peripheral a-adrenoceptors in the cardiovascular system. *Pharmacol Biochem Behav.* 1985;22:827–833.

2. Allen K B, Salam A A, Lumsden A B. Acute mesenteric ischemia after cardiopulmonary bypass. *J Vasc Surg*. 1992;16:391–396.
3. Reilly P M Bulkley G B. Vasoactive mediators and splanchnic perfusion. *Crit Care Med*. 1993;21:S55–S68.
4. Schwinn D A, Johnson G I, Page S O, Mosley M J, Wilson K H, Worman N P, Campbell S, Fidock M D, Furness M, Parry-Smith D, Peter B, Bailey D S. Cloning and pharmacological characterization of human alpha$_1$ adrenergic receptors. *J Pharmacol Exper Ther*. 1995;272:134–142.
5. Hieble J P, Bylund D B, Clarke D E, Eikenburg D C, Langer S Z, Lefkowitz R J, Minneman K P, Ruffolo R R, Jr. International union of pharmacology. X. Recommendation for nomenclature of a$_1$-adrenoceptors. *Pharmacol Rev*. 1995;47:267–270.
6. Price D T, Lefkowitz R J, Caron M G, Berkowitz D, Schwinn D A. Localization of mRNA for three distinct a$_1$-adrenergic receptor subtypes in human tissues. *Mol Pharmacol*. 1994;45:171–175.
7. Price D T, Chari R S, Berkowitz D E, Myers W C, Schwinn D A. Expression of a$_1$-adrenergic receptor subtype mRNA in rat tissues and human SK-N-MC neuronal cells. *Mol Pharmacol*. 1994;46:221–226.
8. Graham R M, Perez D M, Hwa J. Piascik M T. a$_1$-adrenergic receptor subtypes. Molecular structure, function, and signaling. *Circ Res*. 1996;78:737–749.
9. Leech C J Faber J. Different a-adrenoceptor subtypes mediate constriction of arterioles and venules. *Amer J Physiol*. 1996;270:H710–H722.
10. Kong J-Q, Taylor D A, Fleming W W. Functional distribution and role of alpha$_1$ adrenoceptor subtypes in the mesenteric vasculature of the rat. *J Pharmacol Exper Ther*. 1994;268:1153–1159.
11. Xin X, Yang N, Eckhart A D, Faber J E. a$_{1D}$-adrenergic receptors and mitogen-activated protein kinase mediate increased protein synthesis by arterial smooth muscle. *Mol Pharmacol*. 1997;51:764–775.
12. Rokosh D G, Stewart A F, Chang K C, Bailey B A, Karliner J S, Camacho S A, Long C S, Simpson P C. a$_1$-adrenergic receptor subtype mRNAs are differentially regulated by a$_1$-adrenergic and other hypertrophic stimuli in cardiac myocytes in culture and in vivo: repression of a$_{1B}$ and a$_{1D}$ but induction of a$_{1C}$. *J Biol Chem*. 1996;271:5839–5843.
13. Hu Z W, Shi X Y, Hoffman B B. Insulin and insulin-like growth factor I differentially induce a$_1$-adrenergic receptor subtype expression in rat vascular smooth muscle cell. *J Clin Invest*. 1996;98:1826–1834.
14. Malloy B J, Price D T, Price R R, Bienstock A M, Dole M K, Funk B L, Donatucci C F, Schwinn D A. a$_1$-adrenergic receptor subtypes in human detrusor. *J Urol*. 1998;160:937–943.
15. Piascik M L, Guarino R D, Smith M S, Soltis E E, Saussy D L, Jr, Perez D M. The specific contribution of the novel alpha$_{1D}$ adrenoceptor to the contraction of vascular smooth muscle. *J Pharmacol Exper Ther*. 1995;275:1583–1589.
16. Johnson S A, Morgan D G, Finch C E. Extensive postmortem stability of RNA from rat and human brain. *J Neurosci Res*. 1986;16:267–280.
17. Sherwin A, Feindel W, Andermann F, Robitaille Y, Guevremont D, Reader T. Stability of a$_1$-adrenoceptors in surgically excised human brain. *Life Sci*. 1986;39:953–958.
18. Little R A Kirkman E. *Cardiovascular control after injury*. Edited by Cooper G J, Dudley H A F, Gann D S, Little R A. Maynard R L. Oxford, ed., 1997, pp.551–563
19. Piascik M T, Hrometz S L, Edelmann S E, Guarino R D, Hadley R W, Brown R D. Immunocytochemical localization of the alpha-1B adrenergic receptor and the contribution of this and other subtypes to vascular smooth muscle contraction. *J Pharmacol Exper Ther*. 1997;283:854–868.
20. Cavalli A, Lattion A-L, Hummier E, Nenniger M, Pedrazzini T. Aubert J-F, Michel M C, Yang M, Lembo G, Vecchione C, Mostardini M, Schmidt A, Beermann F, Cotecchia S. Decreased blood pressure response in mice deficient of the a$_{1b}$-adrenergic receptor. *Proc Natl Acad Sci USA*. 1997;94:11589–11594.
21. Muramatsu I, Kigoshi S, Ohmura T. Subtypes of a$_1$-adrenoceptor involved in noradrenaline induced contractions of rat thoracic aorta and dog carotid artery. *Jap J Pharmacol*. 1991;57:535–544.
22. Suzuki E, Tsujimoto G, Tamura K, Hashimoto K. Two pharmacologically distinct a$_1$-adrenoceptor subtypes in the contraction of rabbit aorta. *Mol Pharmacol*. 1990;38:725–736.
23. Shibata K, Hirasawa A, Foglar R, Ogawa S. Gozoh T. Effects of quinidine and verapamil on human cardiovascular a$_1$-adrenoceptors. *Circulation*. 1998;97:1227–1230.
24. Diehl N L Shreeve S M. Identification of the a$_{1c}$-adrenoceptor in rabbit arteries and the human saphenous vein using the polymerase chain reaction. *Eur J Pharmacol*. 1994;268:393–398.
25. Hatano A, Takahashi H, Tamaki M, Komeyama T, Koizumi T, Takeda M. Pharmacological evidence of distinct a$_1$-adrenoceptor subtypes mediating the contraction of human prostatic urethra and peripheral artery. *Br J Pharmacol*. 1994;113:723–728.
26. Testa R, Guarneri L, Taddei C, Poggesi E, Angelico P, Sartani A, Leonardi A, Gofrit O N, Meretyk S, Caine M. Functional antagonistic activity for Rec 15/2739, a novel a$_1$ antagonist selective for the lower urinary tract, on noradrenaline-induced contraction of human prostate and mesenteric artery. *J Pharmacol Exper Ther*. 1998;277:1237–1246.
27. Gurdal H, Tilakaratne N, Brown R D, Fonseca M, Friedman E, Johnson M D. The expression of alpha$_1$ adrenoceptor subtypes changes with age in the rat aorta. *J Pharmacol Exper Ther*. 1995;275:1656–1662.
28. Xu K M, Tang F, Han C. Alterations of mRNA levels of a$_1$-adrenoceptor subtypes with maturation and ageing in different rat blood vessels. *Clin Exper Pharmacol Physiol*. 1997;24:415–417.
29. Shaul P W, Magness R R, Muntz K H, DeBeltz D, Buja L M. a$_1$-adrenergic receptors in pulmonary and systemic vascular smooth muscle. *Circ Res*. 1990;67:1193–1200.
30. Ibarra M, Terron J A, Lopez-Guerrero J J, Villalobos-Molina R. Evidence of an age-dependent functional expression of a$_{1D}$-adrenoceptor in the rat vasculature. *Eur J Pharmacol*. 1997;322:221–224.
31. O'Connor G T, Plume S K, Olmstead E M, Coffin L H, Morton J R, Maloney C T, Nowicki E R, Levy D G, Tryzelear J F, Hernandez. F, Adrian L, Casey K J, Bundy D, Soule D N, Marrin C A S, Nugent W C, Charlesworth D C, Clough R, Katz S, Leavirt B J, Wennberg J E. Multivariate prediction of in-hospital mortality associated with coronary artery bypass graft surgery. *Circulation*. 1992;85:2110–2118.
32. Christenson J T, Schmuziger M. Maurice J, Simonet F, Velebit V. Gastrointestinal complications after coronary artery bypass grafting. *J Thorac Cardiovasc Surg*. 1994:108:899–906.
33. Barnett M G, Swartz M T, Peterson G J, Naunheim K S, Pennington D G, Vaca K J, Fiore A C, McBride L R. Peigh P, Willman VLea. Vascular complications from intraaortic balloons: risk analysis. *J Vasc Surg.* 1995;19:81–87.

34. Buzelin J M, Fonteyne E, Kontturi M. Witjes W P J, Khan A. Comparison of tamsulosin with alfuzosin in the treatment of patients with lower urinary tract symptoms suggestive of bladder outlet obstruction (symptomatic benign prostatic hyperplasia). *Br J Urol.* 1997;80:597–605.

All documents cited above are hereby incorporated in their entirety by reference.

One skilled in the art will appreciate from a reading of this disclosure that various changes in form and detail can be made without departing from the true scope of the invention.

What is claimed is:

1. A method of preventing restenosis after myocardial infarction and reperfusion comprising administering to a human patient in need of such prevention an $\alpha_{1a}$-adrenergic receptor ($\alpha_{1a}$-AR) selective antagonist in an amount sufficient to effect said prevention.

2. A method of preventing restenosis after myocardial infarction and reperfusion comprising administering to a human patient in need of such prevention an $\alpha_{1a}/\alpha_{1d}$-AR selective antagonist in an amount sufficient to effect said prevention.

3. A method of preventing restenosis after myocardial infarction and reperfusion comprising administering to a human patient in need of such prevention an $\alpha_{1a}$-adrenergic receptor ($\alpha_{1a}$-AR) selective antagonist in an amount sufficient to effect said prevention, wherein said antagonist is 5-MU.

4. A method of preventing restenosis after myocardial infarction and reperfusion comprising administering to a human patient in need of such prevention an $\alpha_{1a}/\alpha_{1d}$-AR selective antagonist in an amount sufficient to effect said prevention, wherein said antagonist is BMY7378.

* * * * *